(12) United States Patent
Hofmann et al.

(10) Patent No.: US 6,748,265 B2
(45) Date of Patent: Jun. 8, 2004

(54) ELECTRODE APPARATUS AND METHOD FOR THE DELIVERY OF DRUGS AND GENES INTO TISSUE

(75) Inventors: Günter A. Hofmann, San Diego, CA (US); Dietmar P. Rabussay, Solana Beach, CA (US); Zei Zhang, San Diego, CA (US)

(73) Assignee: Genetronics, Inc., San Diego, CA (US)

( * ) Notice: Subject to any disclaimer, the term of this patent is extended or adjusted under 35 U.S.C. 154(b) by 0 days.

(21) Appl. No.: 09/847,468

(22) Filed: May 2, 2001

(65) Prior Publication Data

US 2002/0165481 A1 Nov. 7, 2002

Related U.S. Application Data

(63) Continuation-in-part of application No. 09/134,245, filed on Aug. 14, 1998, now Pat. No. 6,192,270.

(51) Int. Cl.[7] .............................. A61N 1/30; A61N 1/00
(52) U.S. Cl. ......................................... 604/20; 607/152
(58) Field of Search ...................... 604/20–21; 307/1–3, 307/72, 149, 152

(56) References Cited

U.S. PATENT DOCUMENTS

| | | |
|---|---|---|
| 4,950,229 A | 8/1990 | Sage, Jr. |
| 5,053,001 A | 10/1991 | Reller et al. |
| 5,318,514 A | 6/1994 | Hofmann |
| 5,380,272 A | 1/1995 | Gross |
| 5,582,586 A | 12/1996 | Tachibana et al. |
| 5,618,265 A | 4/1997 | Myers et al. |
| 5,667,487 A | 9/1997 | Henley |
| 5,704,908 A | 1/1998 | Hofmann et al. |
| 5,711,761 A | 1/1998 | Untereker et al. |
| 5,869,326 A | 2/1999 | Hofmann |
| 5,944,685 A | 8/1999 | Muroki |
| 6,009,345 A | 12/1999 | Hofmann |
| 6,192,270 B1 * | 2/2001 | Hofmann et al. .............. 604/20 |

FOREIGN PATENT DOCUMENTS

| | | |
|---|---|---|
| EP | 0 337 642 A2 | 10/1989 |
| EP | 0 547 482 A1 | 6/1993 |
| WO | WO 95/26781 | 10/1995 |
| WO | WO 96/00111 | 1/1996 |
| WO | WO 97/04832 | 2/1997 |

* cited by examiner

Primary Examiner—Manuel Mendez
(74) Attorney, Agent, or Firm—BioTechnology Law Group (57) ABSTRACT

An electrode assembly for an apparatus for trans-surface molecular includes a non-conductive carrier having a proximal surface, a distal surface, and a plurality of through holes from the proximal surface to the distal surface, a plurality of first electrodes disposed on the proximal surface, a first conductor disposed on at least a first portion of the distal surface and extending through at least a first portion of the plurality of through holes and connected to the first electrodes on the proximal surface, a plurality of second electrodes disposed on the proximal surface, and a second conductor disposed on at least a second portion of the distal surface and extending through at least a second portion of the plurality of through holes and connected to the second electrodes on the proximal surface, wherein the first electrodes and the second electrodes are configured and disposed in closely spaced relation on the proximal surface for engaging the tissue surface and applying an electric field.

12 Claims, 6 Drawing Sheets

ELECTRODE APPARATUS AND METHOD FOR THE DELIVERY OF DRUGS AND GENES INTO TISSUE

RELATED APPLICATIONS

This application is a continuation-in-part application and claims priority under 35 U.S.C. §120 from U.S. application Ser. No. 09/134,245, filed Aug. 14, 1998, now U.S. Pat. No. 6,192,270 which is incorporated herein by reference in its entirety.

BACKGROUND OF THE INVENTION

The present invention relates generally to electroporation for drug and gene delivery and pertains more particularly to an electrode assembly for an apparatus for and a method of trans-surface delivery of genes, drugs, and other molecules through tissue surfaces for both therapeutic and cosmetic purposes.

The medical community has in recent years been investigating electroporation as a method of trans-surface delivery of drugs, genes such as DNA, portions of DNA, chemical agents, or other molecules without physical penetration or invasion of the tissue surface. This method can be used for the application of molecules for the therapeutic treatment of cancer or for cosmetic treatment of skin blemishes and abnormalities such as wrinkles and age spots. It can also be used for gene therapy. This method involves the electroporation of the tissue surface through the application of an electrical field by means of electrodes on the tissue surface. Electroporation can make tissue permeable to enable the molecules to pass through the tissue surface and more readily enter the tissue. Electroporation can also make cell tissue permeable to enable the molecules to enter preselected cells in the tissue without damaging them.

The molecules to be introduced into the cells are placed in close proximity to the cells, either in the interstitial tissue surrounding the cells or in a fluid medium containing the cells. The field is applied at a predetermined strength and duration in order to make the walls of the tissue surface transiently permeable to permit the molecules to pass through the tissue surface into the underlying tissue.

The voltage that must be applied to induce electroporation is proportional to the distance between the electrodes. When the space between the electrodes is too great, the generated electric field penetrates deep into the tissue where it causes unpleasant nerve and muscle reaction. The applicants have discovered electrode arrays and configurations that maximize the field strength and reduce the unpleasant nerve and muscle reaction.

Electroporation can be carried out by a sophisticated electroporation system having programmable power sequence and duration programmed in. For example, a suitable system is disclosed in U.S. Pat. No. 5,869,326 issued Feb. 9, 1999 entitled ELECTROPORATION EMPLOYING USER-CONFIGURED PULSING SCHEME, which is incorporated herein by reference as though fully set forth. Broadly, that invention concerns an electroporation apparatus for and method of generating and applying an electric field according to a user-specified pulsing scheme. One example of such a pulsing scheme includes a low voltage pulse of a first duration, immediately followed by a high voltage pulse of a second duration, and immediately followed by a low voltage pulse of a third duration. The low voltage field acts to accumulate molecules at the tissue surface, the appropriately high voltage field acts to create an opening in the tissue surface, and the final low voltage field acts to move the molecules through the tissue surface.

While electroporation provides new pathways through the tissue surface for passages of molecules, it does not provide a needed driving force to those molecules to move them through the tissue surface or through the tissue to the cell site. As a result, it is desirable to combine electroporation with techniques for providing a driving force. Iontophoresis alone, wherein low voltage is applied between widely spaced electrodes for a long period of time, can transport charged molecules through existing pathways such as hair follicles and sweat glands. However, the volumes of molecules transported for a unit of time is very small, and insufficient for many applications. Combining electroporation and iontophoresis can increase the amount transported initially while the created pathways are open. The paths created by the electroporation stay open for a only short period of time and then close.

One example of a surface for the trans-surface delivery of molecules is the skin or the stratum corneum (SC). The SC consists of a thin layer of dead cells with a high electrical resistance which presents a major obstacle to the administration of drugs and genes transdermally. However, this layer can be perforated by the administration of short high voltage pulses, which create a dielectric breakdown of the SC forming pores which can allow the passage of molecules.

There is a need for improved electrodes that maximize areas of desired field strength for tissue surfaces to which to apply electroporation which surfaces vary by their size, shape, location, porosity, and accessability, among others. It is desirable that an electrode assembly for an apparatus for and a method of trans-surface molecular delivery be available to efficiently accommodate a wide variety of these tissue surfaces.

SUMMARY AND OBJECTS OF THE INVENTION

It is the primary object of the present invention to provide an improved electrode assembly for an apparatus for and a method of trans-surface molecular delivery which maximize areas of desired field strength for tissue surfaces to which to apply electroporation.

In accordance with the primary aspect of the present invention, electrodes configured to apply to tissue surface are configured to minimize the conductive areas and areas of low field strength while maximizing the areas of desired field strength.

In accordance with the method molecules are brought into physical contact with the tissue surface, an electrode is contacted with the tissue surface, and an electric field is applied to the tissue surface by means of the electrode. This forms pores in the tissue surface. Then a driving force is applied to the tissue surface forcing the molecules through the tissue surface into the underlying tissue.

BRIEF DESCRIPTION OF THE DRAWINGS

The above and other objects and advantages of the present invention will be appreciated from the following specification when read in conjunction with the accompanying drawings wherein.

DETAILED DESCRIPTION OF THE PREFERRED EMBODIMENTS

The present invention was devised to provide an improved electrode assembly for an apparatus for and a method of trans-surface molecular delivery that can accommodate a wide variety of tissue surfaces that vary by their size, shape, location, porosity, and accessability, among others. One example of a surface for the trans-surface delivery of molecules is the skin or the stratum corneum (SC). The SC consists of a thin layer of dead cells with a high electrical resistance which presents a major obstacle to the administration of drugs and genes transdermally. However, this layer can be perforated by the administration of short high voltage pulses, which create a dielectric breakdown of the SC forming pores which can allow the passage of molecules.

Iontophoresis alone, wherein low voltage is applied between widely spaced electrodes for a long period of time, can transport charged molecules through existing pathways such as hair follicles and sweat glands. However, the volumes of molecules transported for a unit of time is very small, and insufficient for many applications. As a result, it is desirable to combine electroporation with techniques for providing a driving force such as pressure, ultrasound, electroincorporation, and iontophoresis. First, pressure can be applied mechanically by pressing on the electrode assembly with any suitable means for applying a reasonably uniform pressure over the desired area. Second, ultrasound can be applied by an ultrasound source. Third, electroincorporation can be applied to transport molecules through the tissue surface into the tissue. Fourth, iontophoresis can be applied as the driving force.

A combination of electroporation and iontophoresis can be carried out by a sophisticated combination system having two electrode assemblies and two power supplies. For example, a suitable system is disclosed in U.S. Pat. No. 6,009,345 issued Dec. 28, 1999, entitled METHOD AND APPARATUS FOR A COMBINATION OF ELECTROPORATION AND IONTOPHORESIS FOR THE DELIVERY OF DRUGS AND GENES, which is incorporated herein by reference as though fully set forth. Broadly, one example of the apparatus disclosed in the above referenced patent and for which the electrodes of the invention is shown here in FIG. 1.

Figure 1:
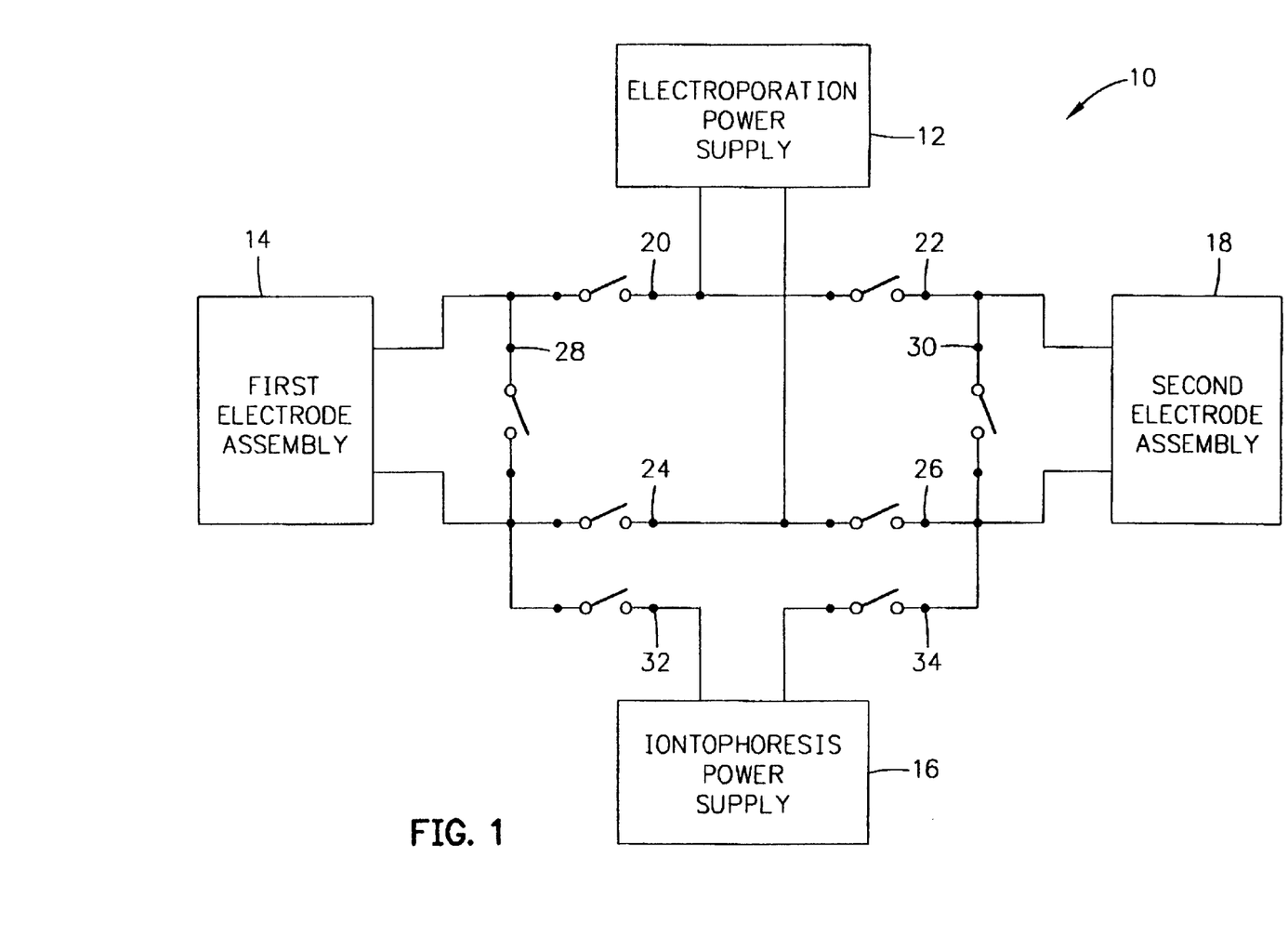
FIG. 1 is a schematic diagram showing a combined electroporation and iontophoresis apparatus.

Turning first to FIG. 1, a schematic diagram of a combined electroporation and iontophoresis apparatus 10 is shown. The apparatus 10 includes an electroporation power supply 12, a first electrode assembly 14, an iontophoresis power supply 16, and a second electrode assembly 18 all of which are connected together by a network of switches (20, 22, 24, 26, 28, 30, 32, and 34) and conductors as shown. In one embodiment, the first and second electrode assemblies 14, 18 each include a first and a second electrode (not shown) which are in closely spaced relation to each other. In another embodiment one electrode assembly includes a first and second electrode and the other includes a single electrode. It is contemplated that the electrode assemblies will be in the form of a patch which may be worn for a period of time and powered by a small battery pack.

In operation, electroporation and iontophoresis of the tissue surface are performed sequentially. During electroporation, the electroporation power supply 12 is connected to the first electrode assembly 14 and the second electrode assembly 18 by closing switches 20, 22, 24, and 26 while switches 28, 30, 32, and 34 are held open. During iontophoresis, the iontophoresis power supply 16 is connected to the first electrode assembly 14 and the second electrode assembly 18 by closing switches 28, 30, 32, and 34 while switches 20, 22, 24, and 26 are held open.

Alternatively, the second electrode assembly 18 could include only one electrode (not shown). In such an apparatus 10, switches 22 and 26 would remain permanently open and switch 30 would remain permanently closed. During electroporation, the electroporation power supply 12 is connected to the first electrode assembly 14 by closing switches 20 and 24 while switches 28, 32, and 34 are held open. During iontophoresis, the iontophoresis power supply 16 is connected to the first electrode assembly 14 and the second electrode assembly 18 by closing switches 28, 32, and 34 while switches 20 and 24 are held open. In this instance only the first electrode assembly 14 participates in the electroporation and both participate in iontophoresis.

In one embodiment of the apparatus 10, the first and second electrode assemblies 14, 18 are each a special patch that is applied to spaced areas of the tissue surface. A solution containing the drugs or genes to be introduced can be contained in the patch which also includes the electrode structure to create the electric field for electroporation. The electrode structure can be inside or on a surface of the patch and the patch would preferably contain a reservoir. The electrode structure is connected to two conductors outside of the patch so that the electroporation and iontophoresis power supplies 12, 16 can be connected momentarily to these outside conductors to provide a voltage pulse. The patch is preferably provided with an adhesive border to adhere it to the tissue surface. The tissue engaging area of the patch is also preferably provided with a protective cover which can be peeled off before adhering the patch to the tissue surface. This would also allow fluid carrying drugs or genes to pass through openings in the patch to the tissue surface.

When iontophoresis is used as the driving force, an electrophoresis electrode is preferably separate from the electroporation electrodes and may also be part of the patch and positioned above the electroporation electrodes. The iontophoresis return electrode may also be remote from the patch electrode assembly or may surround it. An electroporation pulse is first applied to the appropriate electrodes to open pores in the tissue surface. An iontophoresis current is then applied between the appropriate electrodes to draw the drugs or genes through the pores.

Figure 2:
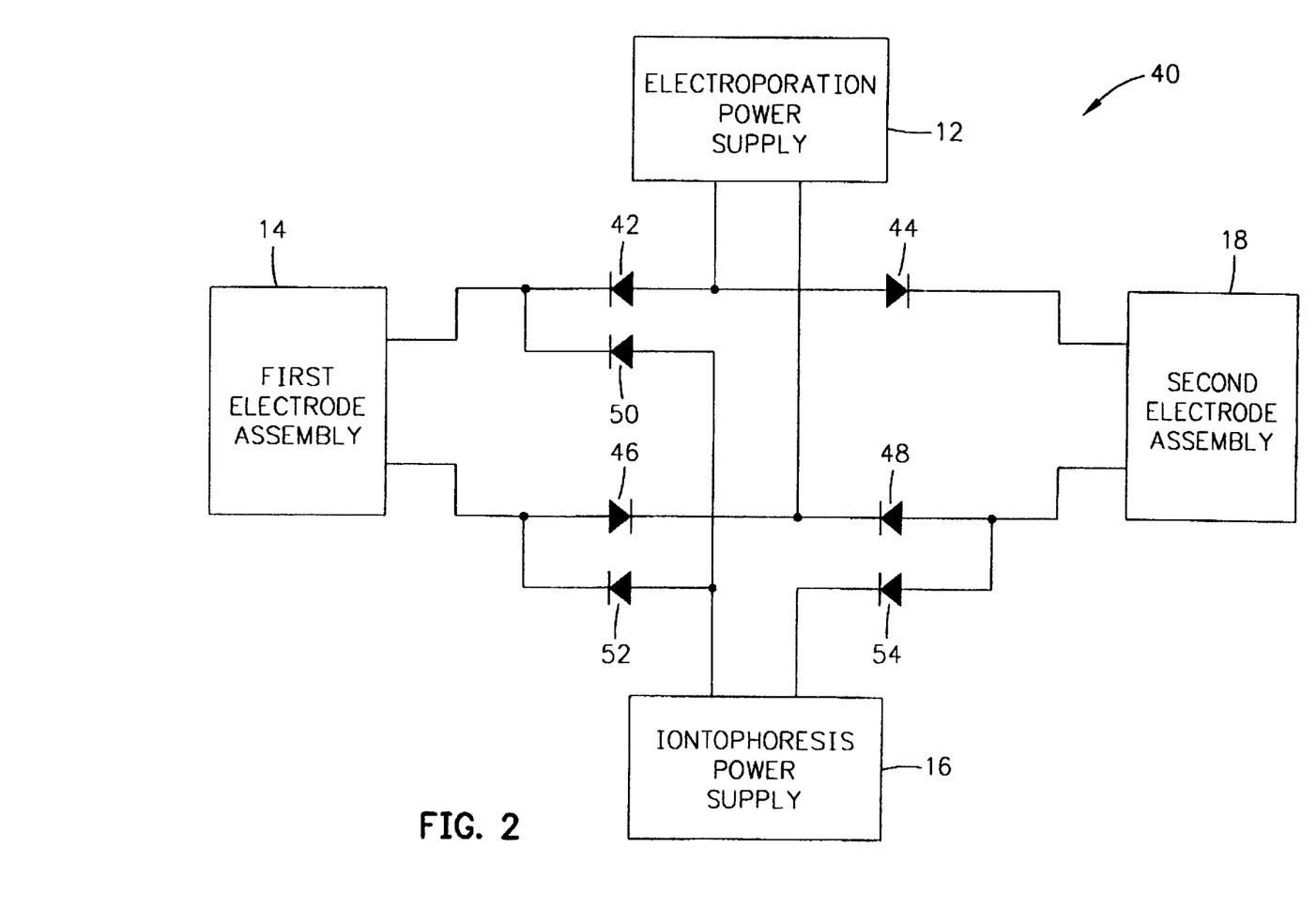
FIG. 2 is schematic diagram showing an alternate embodiment of a combined electroporation and iontophoresis apparatus.

Turning now to FIG. 2, a schematic diagram of a second or alternate embodiment of a combined electroporation and iontophoresis apparatus 40 is shown. The apparatus 40 includes an electroporation power supply 12, a first electrode assembly 14, an iontophoresis power supply 16, and a second electrode assembly 18 all of which are connected together by a network of diodes (42, 44, 46, 48, 50, 52, and 54) and conductors as shown. The first and second electrode assemblies 14, 18 each include a first and a second electrode (not shown) which are in closely spaced relation to each other.

As in the prior embodiment discussed above, in operation, electroporation and iontophoresis of the tissue surface are performed sequentially. Unlike the prior embodiment, no switches are involved here. During electroporation, the electroporation power supply 12 is energized and the iontophoresis power supply 16 is off. During iontophoresis, the iontophoresis power supply 16 is energized and the electroporation power supply 12 is off. Otherwise, the apparatus of FIG. 2 can be used in the same manner as the apparatus of FIG. 1. This includes the use of the subsequently described electrode assemblies described with respect to FIGS. 3, 4, and 5 below.

Figure 3:
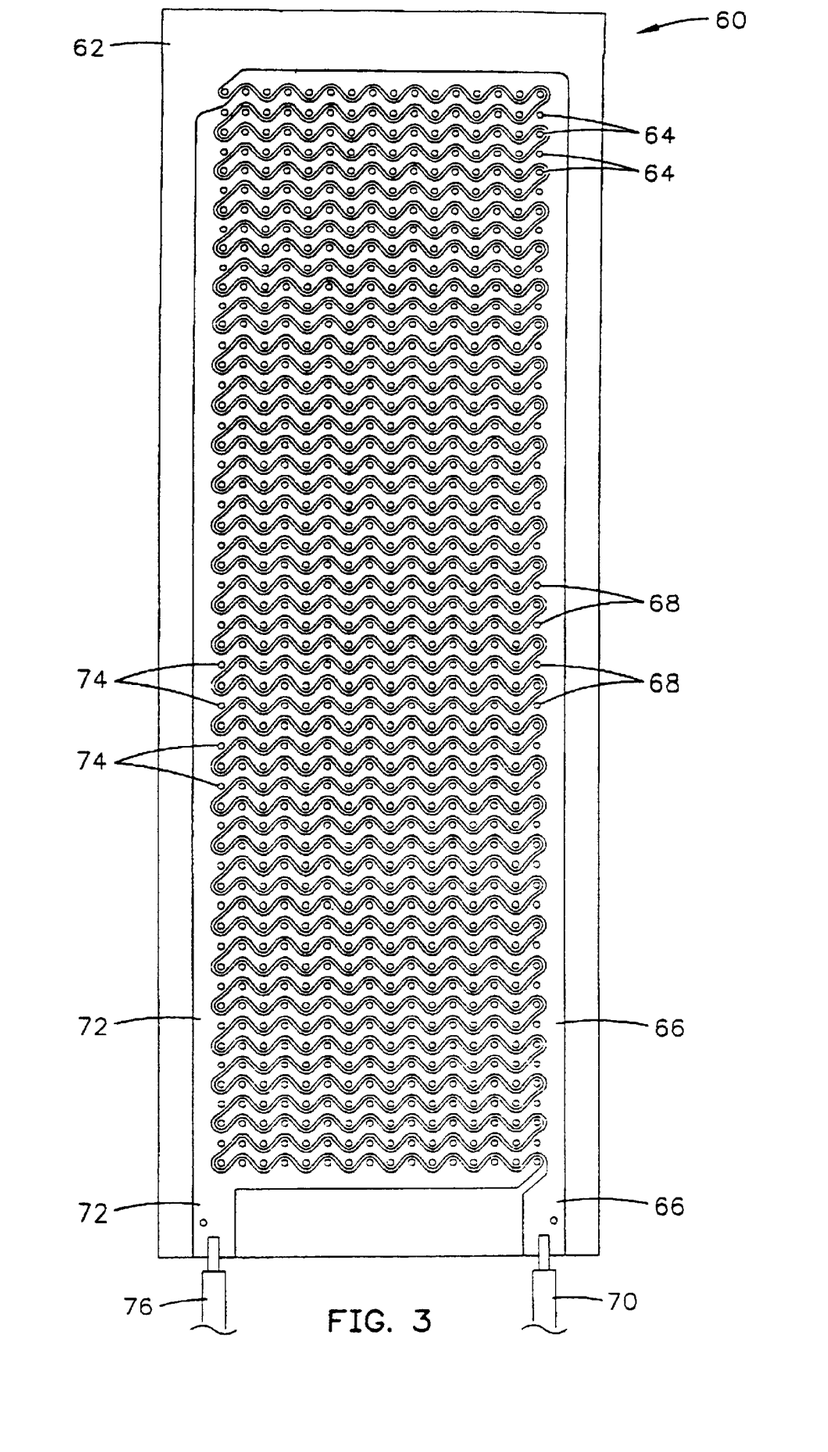
FIG. 3 is a plan view of a top or distal side of an electrode assembly according to the present invention.

Turning now to FIG. 3, a view of a distal or back side of an electrode assembly 60 according to a preferred embodiment of the present invention is shown. The electrode assembly 60 could be substituted for either or both of the first and second electrode assemblies 14, 18 shown in FIG. 1. The electrode assembly 60 includes a non-conductive carrier 62 which has a plurality of through holes 64 which run from the distal side to a proximal side (see FIG. 4). Disposed on the distal side is a first conductor 66. The first conductor 66 extends through a first portion 68 of the plurality of through holes 64 and onto the proximal side of the carrier and connect to a first plurality of electrodes.

A first lead or conductor 70 is coupled to the first conductor 86 for connecting to a power supply. Also disposed on the distal side is a second conductor 72. The second conductor 72 extends through a second portion 74 of the plurality of through holes 64 and onto the proximal side and connect to a second plurality of electrodes. A second lead or conductor 76 is coupled to the second conductor 72 for connecting to a power supply. Optionally, an insulating barrier (not shown) may be disposed on the distal side between the first conductor 66 and the second conductor 72.

Figure 4:
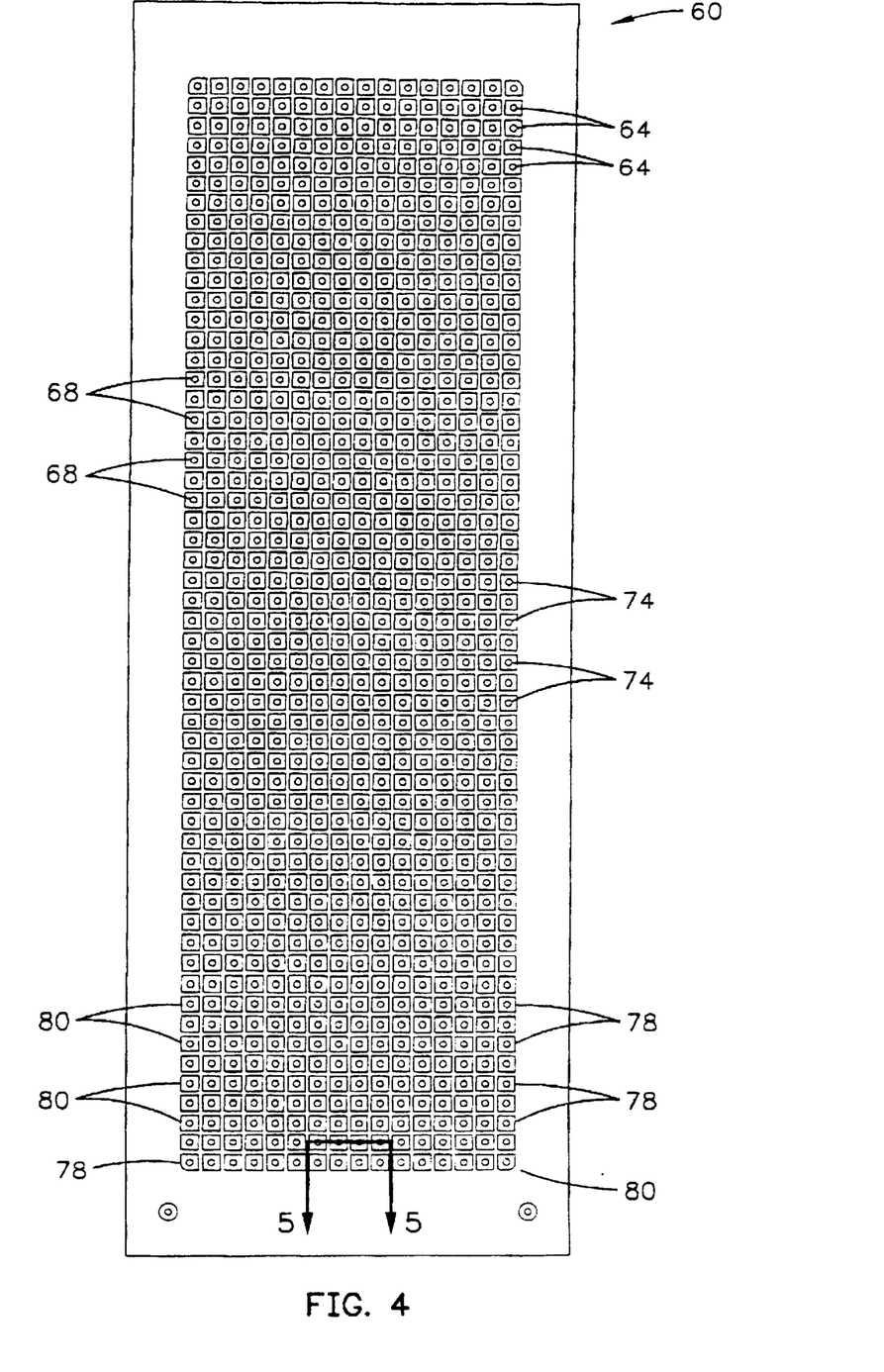
FIG. 4 is a plan view of a face or proximal side of an electrode assembly according to the present invention.

Turning now to FIG. 4, a view of a proximal or front side of an electrode assembly 60 according to a preferred embodiment of the present invention is shown. The proximal side is the side of the electrode assembly 60 that would normally be placed near or against the tissue surface (not shown) that is to be the subject of electroporation. Corresponding to the distal side (see FIG. 4), the proximal side has the plurality of through holes 64. The first conductor 66 extends through the first portion 68 of the plurality of through holes 64 from the distal side and connect to the first plurality of electrodes 78. The second conductor 72 extends through the second portion 74 of the plurality of through holes 64 from the distal side and connect to the second plurality of electrodes 80. Close inspection will reveal that the first electrode 66 and the second electrode 72 alternate in both the vertical and horizontal directions. Each electrode in the inner rows are surrounded by four other electrodes of opposite polarity. The preferred shape of the electrodes shown in this embodiment is that of a square. This construction provides an array of electrodes configured to provide a lot of edge area maximizing the edge effect. The area between the edges of the adjacent electrodes will be exposed to the desired field strength.

The electrodes are separated by an insulation structure forming a grid structure surrounding each electrode and extending above or beyond the surfaces thereof. This insulation forces the electrical field to penetrate the tissue surface rather than conduct along the tissue surface. This arrangement is particularly desirable where the tissue surface is moist. Optionally, an insulating barrier (not shown) may be disposed on the proximal side between the first conductor 66 and the second conductor 72. Where the tissue surface is to be dry, the insulation barrier may preferably be slightly below the electrode surface to provide more area contact of the electrode surface with the tissue surface.

Figure 5:
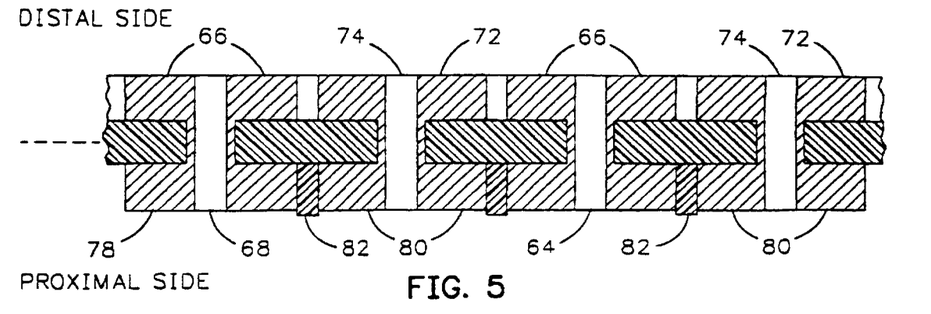
FIG. 5 is an enlarged broken cross-sectional view of an electrode assembly according to the present invention taken through the line 5—5 of FIG. 4.

Turning now to FIG. 5, an enlarged broken cross-sectional view of an electrode assembly 60 according to a second preferred embodiment of the present invention taken through the line 5—5 of FIG. 4 is shown. Of particular interest in this view is that one can see that the first conductor 66 extends through the first portion 68 of the plurality of through holes 64 and onto the proximal side. Further, one can see that the second conductor 72 extends through the second portion 74 of the plurality of through holes 64 and onto the proximal side.

The illustrated embodiment of the electrode assembly 60 shown in FIGS. 3, 4, and 5 is purely for illustration purposes. The final configuration will depend on the particular application. As a result, the overall size, shape, and thickness may vary. The size, shape, number, and location of the plurality of through holes 64 may vary. The shape, thickness, and location of the first electrode 78 and the second electrode 80 may vary.

In the preferred embodiment, the electrode assembly 60 is manufactured using the same techniques used to create printed circuit boards. The carrier 62 is a thin flexible film which allows the electrode assembly 60 to be contoured to the tissue surface which generally has an irregular shape. In one embodiment, the plurality of through holes 64 are provided in part so that drugs and genes can be supplied from a reservoir (not shown) on the distal side and pass through the plurality of through holes 64 to the tissue surface. The first electrode 78 and the second electrode 80 are closely spaced so as to limit the penetration of the field to a shallow layer of the tissue and to maximize the edge effect. In the preferred embodiment, the electrode assembly 60 is manufactured using the same techniques used to create printed circuit boards. The carrier 62 is a thin flexible film which allows the electrode assembly 640 to be contoured to the tissue surface which generally has an irregular shape. In one embodiment, the plurality of through holes 64 are provided in part so that drugs and genes can be supplied from a reservoir (not shown) on the distal side and pass through the plurality of through holes 64 to the tissue surface. The insulating barrier 82 is a solder mask which reduces the flow of current directly between the first electrode 78 and the second electrode 80 across the tissue surface. However, the first electrode 46 and the second electrode 54 are closely spaced so as to limit the penetration of the field to a shallow layer of the tissue.

Figure 6:
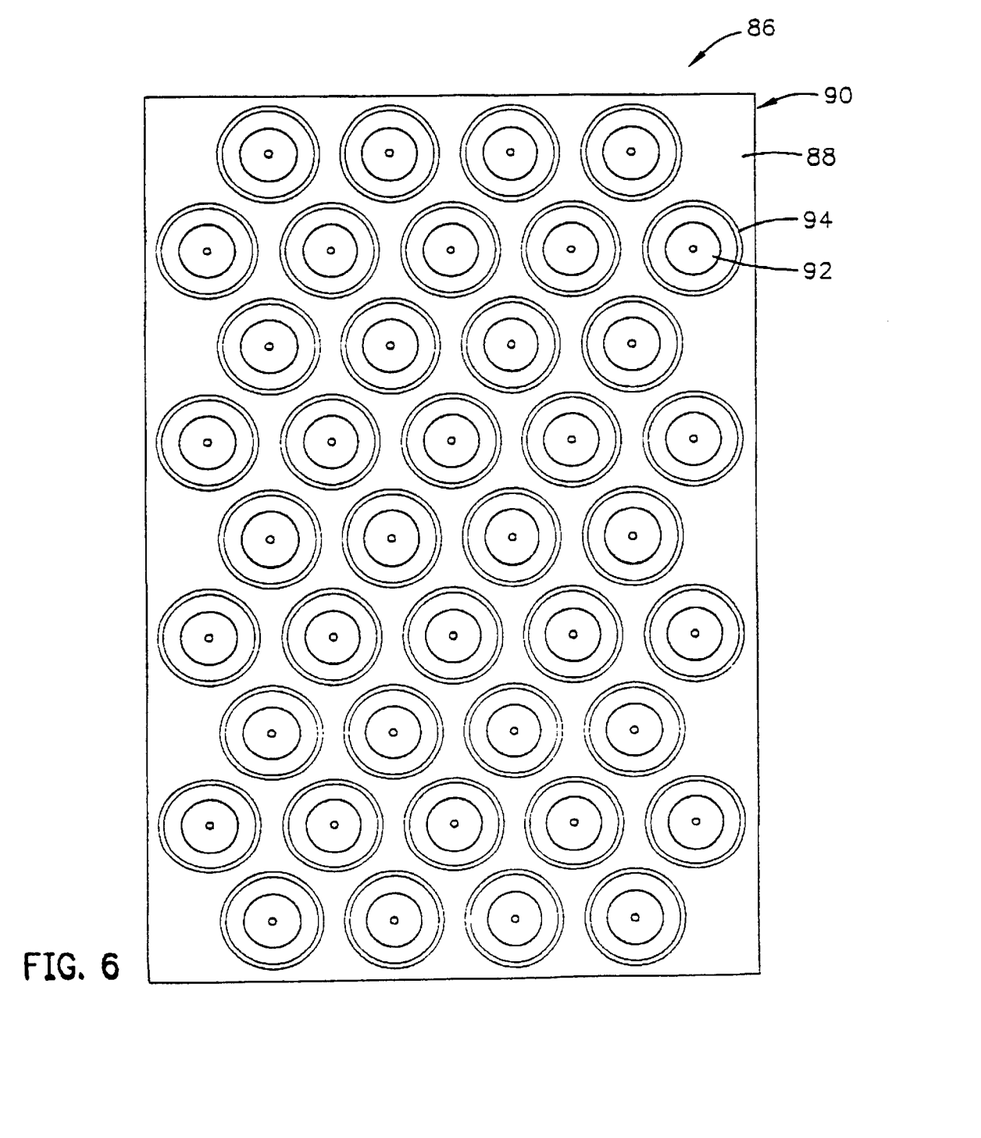
FIG. 6 is a view of a face or proximal side of an alternate embodiment of an electrode assembly according to the present invention.

Turning now to FIG. 6, a view of a proximal or front side of an alternate embodiment of an electrode assembly 86 according to an embodiment of the present invention is shown. The proximal side is the side of the electrode assembly 86 that would normally be placed near or against the tissue surface (not shown) that is to be the subject of electroporation. The electrode assembly comprises an insulating carrier 88 of a thin flexible material on which is mounted a plurality of electrodes. An array of electrode units 90 are positioned in rows throughout the face of the carrier. Each electrode unit for the purposes of this description comprises a pair of electrodes positioned to to be connected in opposite polarity and act in opposition to one another. The electrode units each comprise a first or center electrode 92 of a circular configuration, each surrounded by an electrode 94 of a ring or doughnut configuration. These are configured to minimize the conductive areas and areas of low field strength while maximizing the areas of desired high field strength.

The goal of the electrode configuration is to minimize the conductive areas and the areas of low field strength while maximizing the areas of desired field strength. E.g., the area between the center electrodes and the ring electrodes will be exposed to the desired field strength, whereas only parts of the area between doughnuts will be exposed to the desired field strength. The minimal area that can be covered by conductive materials is a function of the applied voltage, the specific conductivity of the conductive material, the cross-section of the conductive material and the conductivity of the material (e.g., skin) with which the electrode is intended to be in contact with. Optimization of the electrode design will be based on these considerations. Another consideration is the flatness of the electrode array. If dry skin is to be electroporated, it appears advantageous to have the surface of the conductive material raised by 0.1 to a few mm above the surface of the non-conductive surfaces. If wet skin or the wet surface of another organ is intended to be electroporated, the opposite seems advantageous, i.e., the non-conductive surfaces should be raised relative to the conductive surfaces. In the first case, the raised conductive material will ensure good contact with the dry surface to be electroporated (e.g., dry skin). In the latter case the raised insulating material will help to minimize leakage current between electrodes via the liquid on the surface to be electroporated.

Figure 7:
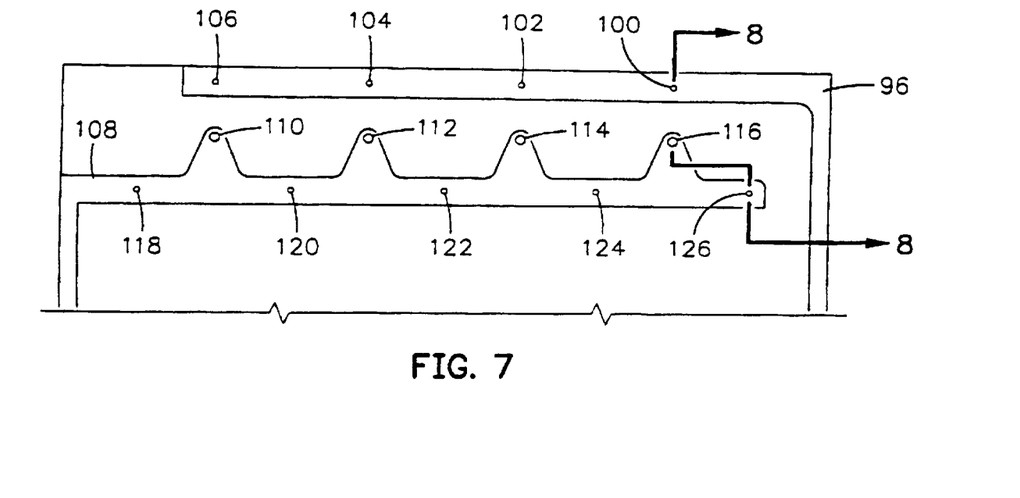
FIG. 7 is a partial top view of a second electrode assembly according to the present invention.
Figure 8:
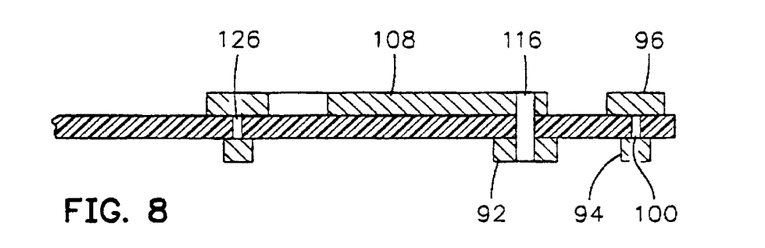
FIG. 8 is an enlarged broken cross-sectional view taken through the line 8—8 of FIG. 7

The connection of conductors to the electrodes may be carried out with a structure of conductors substantially like that of FIG. 3. In one embodiment, the electrodes are connected by a series of conductors as illustrated in FIG. 7. FIG. 7 is a partial view of the distal or back side of the electrode assembly of FIG. 6 showing an exemplary arrangement of conductors to the electrodes on the face of the electrode assembly. A first conductor 96 extends along one end and a side of the carrier and connects via through holes at 100, 102, 104 and 106 to the ring electrodes 94 of the end row of electrode units. A second conductor extends across the carrier and connects via open through holes 110, 112, 114 and 116 to the center electrodes 92 of the first row of electrode units. The second conductor also connects via through holes 118, 120, 122, 124 and 126 to the ring electrodes of the next row of electrode units. It will be seen that the center electrodes of the units will be of different polarity than the ring electrode of that unit. Also the center electrode of one row will have the same polarity as the ring electrode of an adjacent row of electrode units. It will be appreciated that other connection arrangements may be made to achieve the object of the invention.

Figure 9:
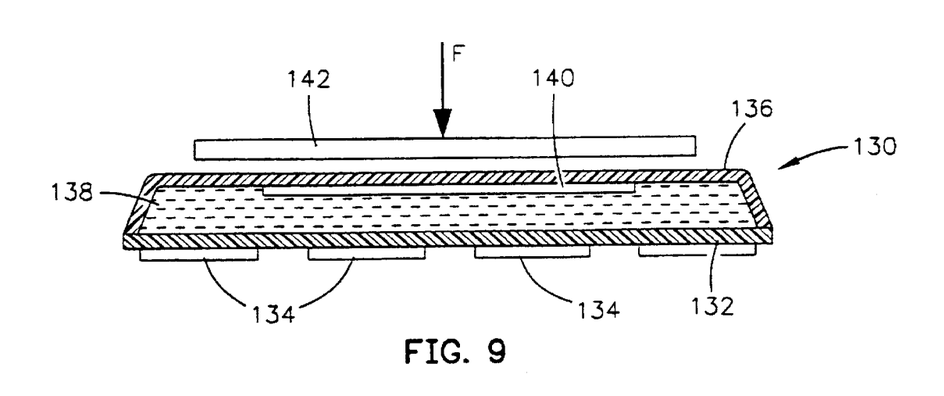
FIG. 9 is side elevation section view a combined electrode and reservoir embodiment of the invention.

The electrode assemblies herein described are designed to be incorporated into a patch as illustrated in FIG. 9 to be applied to the tissue surface such as by an adhesive and powered such as by a battery pack. An exemplary patch designated generally at 130 comprises a carrier 132 on which is mounted electrodes 134 with conductors as described in previous embodiments above. A bladder 136 forms a reservoir 138 above the electrode assembly and contains a fluid medium to carry molecules to be delivered to the tissue. A driving force F is applied to the fluid in the reservoir to force the molecules from the reservoir into the tissue. If the driving force is iontophoresis, an iontophoresis electrode 140 is positioned above the electrodes 134 and a return iontophoresis electrode can be remote from the patch or may surround it.

Alternate force applying means 142 can be an ultrasonic transducer or other suitable means for forcing the fluid from the reservoir into the tissue.

The techniques of electroincorporation may also be used with the herein detailed system and electrodes for the delivery of molecules across tissue surface. This technique is more fully disclosed in U.S. Pat. Nos. 5,462,520 and 5,464,386, which are incorporated herein by reference as though fully set forth.

While the invention has been illustrated and described by means of specific embodiments, it is to be understood that numerous changes and modifications may be made therein without departing from the spirit and scope of the invention as defined in the appended claims.

What is claimed is:

1. An apparatus for trans-surface molecular delivery, comprising:
   a first electrode assembly, comprising:
      a non-conductive carrier having a proximal surface, a distal surface, and a plurality of through holes from the proximal surface to the distal surface;
      a plurality of first electrodes disposed on at least a first portion of the proximal surface;
      a first conductor disposed on said distal surface and extending through at least a first portion of the plurality of through holes and connected to the plurality of first electrodes; and
      a plurality of second electrodes disposed on at least a second portion of the of the proximal surface;
      a second conductor disposed on said distal surface and extending through at least a second portion of the plurality of through holes and connected to the plurality of second electrodes;
   wherein the first electrodes are in closely spaced relation with the second electrodes on the proximal surface for engaging the tissue surface and applying an electric field;
   a first power supply connected to the first electrode assembly for applying a pulsed electric field of sufficient amplitude to induce pores in the tissue surface; and
   means for driving molecules through pores in the tissue surface.

2. The apparatus according to claim 1 wherein means for driving comprises: a second electrode assembly spaced from the first electrode assembly and comprising at least one of an anode and a cathode; and a second power supply connected to the first electrode assembly and the second electrode assembly for applying a low voltage continuous electric field of a preselected polarity and sufficient amplitude to induce migration of molecules through pores in the tissue surface.

3. The apparatus according to claim 2, wherein said first power supply and said second power supply comprising:
   an electroporation power supply having a first contact and a second contact wherein a pulsed electric field of sufficient amplitude to induce pores in the tissue surface is applied;
   an iontophoresis power supply having a first contact and a second contact wherein a low voltage continuous electric field of a preselected polarity and sufficient amplitude to induce migration of molecules through pores in the tissue surface is applied;
   a first electrode assembly having a first contact and a second contact;
   a second electrode assembly having a first contact and a second contact;

a first diode having an input connected to the first contact of the electroporation power supply and an output connected to the first contact of the first electrode assembly;

a second diode having an input connected to the first contact of the electroporation power supply and an output connected to the first contact of the second electrode assembly;

a third diode having an input connected to the second contact of the first electrode assembly and an output connected to the second contact of the electroporation power supply;

a fourth diode having an input connected to the second contact of the second electrode assembly and an output connected to the second contact of the electroporation power supply;

a fifth diode having an input connected to the first contact of the iontophoresis power supply and an output connected to the first contact of the first electrode assembly;

a sixth diode having an input connected to the first contact of the iontophoresis power supply and an output connected to the second contact of the first electrode assembly; and a seventh diode having an input connected to the second contact of the second electrode assembly and an output connected to the second contact of the iontophoresis power supply.

4. The apparatus according to claim 1 wherein means for driving comprises a pressure source in communication with the tissue surface via the plurality of through holes in the carrier of the first electrode assembly for applying pressure of a sufficient amplitude and duration to induce migration of molecules through pores in the tissue surface.

5. The apparatus according to claim 1 wherein means for driving comprises an ultrasound source for applying ultrasound of a sufficient amplitude and duration to induce migration of molecules through pores in the tissue surface.

6. The apparatus according to claim 1 wherein means for driving comprises means for electroincorporation of molecules for applying electroincorporation of a sufficient amplitude and duration to induce migration of particles containing molecules through pores in the tissue surface.

7. A method of trans-surface molecular delivery, comprising:
providing a first electrode assembly, comprising:
a non-conductive carrier having a proximal surface, a distal surface, and a plurality of through holes from the proximal surface to the distal surface;
a plurality of first electrodes disposed on at least a first portion of the proximal surface;
a first conductor disposed on said distal surface and extending through at least a first portion of the plurality of through holes and connected to the plurality of first electrodes; and
and a plurality of second electrodes disposed on at least a second portion of the proximal surface and in closely spaced relation with the plurality of first electrodes;
engaging a tissue surface with the first electrode assembly;
providing a first power supply connected to the first electrode assembly;
applying a pulsed electric field via the first electrode assembly of sufficient amplitude to induce pores in the tissue surface;
providing means for driving molecules through pores in the tissue surface;
and applying means for driving to induce migration of molecules through pores in the tissue surface.

8. The method according to claim 7 wherein the step of providing means for driving comprises the steps of:
providing a second electrode assembly spaced from the first electrode assembly and comprising at least one of an anode and a cathode; and
providing a second power supply connected to the first electrode assembly and the second electrode assembly, and wherein the step of applying means for driving comprises the step of applying a low voltage continuous electric field of a preselected polarity and sufficient amplitude to induce migration of molecules through pores in the tissue surface.

9. The method according to claim 7 wherein the step of providing means for driving comprises the step of providing a pressure source in communication with the tissue surface via the plurality of through holes in the carrier of the first electrode assembly and wherein the step of applying means for driving comprises the step of applying pressure to the first electrode assembly of a sufficient amplitude and duration to induce migration of molecules through ores in the tissue surface.

10. The method according to claim 7 wherein the step of providing means for driving comprises the step of providing an ultrasound source and wherein the step of applying means for driving comprises the step of applying ultrasound of a sufficient amplitude and duration to induce migration of molecules through pores in the tissue surface.

11. The method according to claim 7 wherein the step of providing means for driving comprises the step of providing means for electroincorporation of molecules and wherein the step of applying means for driving comprises the step of applying means for electroincorporation of a sufficient amplitude and duration to induce migration of particles containing molecules through pores in the tissue surface.

12. An apparatus for trans-surface molecular delivery, comprising:
an electroporation power supply having a first contact and a second contact wherein a pulsed electric field of sufficient amplitude to induce pores in the tissue surface is applied;
an iontophoresis power supply having a first contact and a second contact wherein a low voltage continuous electric field of a preselected polarity and sufficient amplitude to induce migration of molecules through pores in the tissue surface is applied;
a first electrode assembly having a first contact and a second contact;
a second electrode assembly having a first contact and a second contact;
a first diode having an input connected to the first contact of the electroporation power supply and an output connected to the first contact of the first electrode assembly;
a second diode having an input connected to the first contact of the electroporation power supply and an output connected to the first contact of the second electrode assembly;
a third diode having an input connected to the second contact of the first electrode assembly and an output connected to the second contact of the electroporation power supply;
a fourth diode having an input connected to the second contact of the second electrode assembly and an output connected to the second contact of the electroporation power supply;

a fifth diode having an input connected to the first contact of the iontophoresis power supply and an output connected to the first contact of the first electrode assembly;

a sixth diode having an input connected to the first contact of the iontophoresis power supply and an output connected to the second contact of the first electrode assembly; and a seventh diode having an input connected to the second contact of the second electrode assembly and an output connected to the second contact of the iontophoresis power supply.

* * * * *